United States Patent [19]
Kim et al.

[11] Patent Number: 5,807,572
[45] Date of Patent: Sep. 15, 1998

[54] MULTIVESICULAR LIPOSOMES HAVING A BIOLOGICALLY ACTIVE SUBSTANCE ENCAPSULATED THEREIN IN THE PRESENCE OF A HYDROCHLORIDE

[75] Inventors: Sinil Kim, Solana Beach; Stephen B. Howell, Del Mar, both of Calif.

[73] Assignee: DepoTech Corporation, La Jolla, Calif.

[21] Appl. No.: 473,019

[22] Filed: Jun. 6, 1995

Related U.S. Application Data

[63] Continuation-in-part of Ser. No. 352,342, Dec. 7, 1994, abandoned, which is a continuation of Ser. No. 20,483, Feb. 23, 1993, abandoned, which is a continuation of Ser. No. 709,744, Jun. 3, 1991, abandoned, which is a continuation-in-part of Ser. No. 563,365, Aug. 6, 1990, abandoned, which is a continuation-in-part of Ser. No. 151,553, Feb. 18, 1988, abandoned.

[51] Int. Cl.$^6$ .................................................. A61K 9/127
[52] U.S. Cl. .............................. 424/450; 264/4.1; 264/4.3
[58] Field of Search ............................. 424/450; 264/4.1, 264/4.3

[56] References Cited

U.S. PATENT DOCUMENTS

| | | | |
|---|---|---|---|
| 4,078,052 | 3/1978 | Paphadjopoulos | 424/36 |
| 4,089,801 | 5/1978 | Schneider | 424/450 |
| 4,145,410 | 3/1979 | Sears | 424/19 |
| 4,224,179 | 9/1980 | Schneider | 424/450 |
| 4,235,871 | 11/1980 | Papahadjopoulos et al. | 264/4.1 |
| 4,241,046 | 12/1980 | Papahadjopoulos | 424/450 |
| 4,310,506 | 1/1982 | Baldeschwieler | 424/1 |
| 4,394,372 | 7/1983 | Taylor | 424/450 |
| 4,522,803 | 6/1985 | Lenk et al. | 424/1.1 |
| 4,588,578 | 5/1986 | Fountain et al. | 424/1.1 |
| 4,599,227 | 7/1986 | Dees et al. | 424/38 |
| 4,610,868 | 9/1986 | Fountain et al. | 424/1.1 |
| 4,721,612 | 1/1988 | Janoff | 424/1.1 |
| 4,752,425 | 6/1988 | Martin et al. | 264/4.6 |

(List continued on next page.)

FOREIGN PATENT DOCUMENTS

| | | |
|---|---|---|
| 2050799 | 1/1981 | United Kingdom . |
| 2050287 | 1/1991 | United Kingdom . |

OTHER PUBLICATIONS

Kim et al, BBA 793, p. 801, 1985.
Kim et al, BBA 646, 1 1981.
Crommelin Internat. J. Pharmaceutics 76, p. 79 (1983).
"Topology of Multivesicular Liposomes, a Model Biliquid Foam," *Langmuir* 12:4704–4708, 1996, by M.S. Spencer et al.
Huang, Biochemistry, 8:334–352, 1969, "Studies on Phosphatidylcholine Vesicles formation and Physical characteristics."
Bang, M. Mol. Bio., 13–238–252, 1965, "Diffusion of univalent ions across the lamellae of swollen phospholipids."
Szoka, et al., Ann. Rev. Biophys. Bioeng., 9:465–508, 1980, "Comparative properties and methods of preparation of lipid vesicles (liposomes)."

(List continued on next page.)

*Primary Examiner*—Gollamudi S. Kishore
*Attorney, Agent, or Firm*—Fish & Richardson P.C.

[57] ABSTRACT

Disclosed are multivesicular liposomes containing biologically active substances, the multivesicular liposomes having defined size distribution, adjustable average size, adjustable internal chamber size and number, and a modulated rate of the biologically active substance in contrast to the previous art. The process comprises dissolving a lipid component in volatile organic solvents, adding an immiscible aqueous component containing at least one biologically active substance to be encapsulated, and adding to either or both the organic solvents and the lipid component, a hydrochloride effective to control the release rate of the biologically active substance from the multivesicular liposome, making a water-in-oil emulsion from the two components, immersing the emulsion into a second aqueous component, dividing the emulsion into small solvent spherules which contain even smaller aqueous chambers, and then removing the solvents to give an aqueous suspension of multivesicular liposomes encapsulating biologically active substances.

40 Claims, 1 Drawing Sheet

U.S. PATENT DOCUMENTS

| | | | |
|---|---|---|---|
| 4,769,250 | 9/1988 | Forssen | 424/450 |
| 4,781,871 | 11/1988 | West, III et al. | 264/4.3 |
| 4,920,016 | 4/1990 | Allen et al. | 424/450 |
| 4,975,282 | 12/1990 | Cullis | 424/450 |
| 5,000,959 | 3/1991 | Iga et al. | 424/450 |
| 5,021,200 | 6/1991 | Vanlerberghe et al. | 264/43 |
| 5,077,056 | 12/1991 | Bally et al. | 424/450 |
| 5,204,112 | 4/1993 | Hope et al. | 424/450 |
| 5,334,381 | 8/1994 | Unger et al. | 424/9 |
| 5,334,391 | 8/1994 | Clark et al. | 424/450 |

OTHER PUBLICATIONS

Shakiba, et al., Investigative ophthalmology and visual Science, 34(10):2903–10, 1993 Sep., "Evaluation of retinal toxicity and liposome encapsulation of the Anti–CMV Drug 2'–nor–cyclic GMP."

Frucht–Perry, et al., Cornea, 11(5):393–7, 1992 Sep., "Fibrin–enmeshed tobramycin liposomes: single application topical therapy of pseudomonas . . . ".

Assil, et al., Investigative Ophthalmology and Visual Sciences, 32(13):3216 1991 Dec., Tobramycin liposomes. Single subconjuctival therapy of . . . .

Assil, et al., Investigative Ophthalmology and Visual Science, 32(11):2891 1991 Oct., Liposome suppression of proliferative vitreoretinopathy. Rabbit.

Turski, et al., Magnetic Resonance in Medicine, 7(2):184–96, 1988 Jun., Magnetic resonance imaging of rabbit brain after intracarotid injection.

Skuta, et al., American Journal of Ophthalmology, 103(5):714–16, 1987, May "Filtering surgery in owl monkeys treated with the antimetabolite . . . ."

Assil, et al., Archives of Opthalmology, 105(3):400–3, 1987 Mar., "Multivesicular liposomes. Sustained release of the antimetabolite . . . . "

Barbet, et al., Biochimica et Biophysica Acta, 772(3):347–56, 1984, May 30 "Weat acid–induced release of liposome–encapsulated carboxyfluorescein".

Russack, et al., Ann. Neurol., 34:108–112, 1993, "Quantitative cerebrospin fluid cytology in patients receiving intracavitary chemotherapy."

Kim, et al., J. Clin. Oncol., 11:2186–2193, 1993, Extended cerebrospinal–fluid cytarabine exposure following intrathecal administration of DTC 101.

Kim, Drugs, 46:618–638, 1993, "Liposomes as carriers of cancer chemotherapy: a review."

Kim, Kim, KIm, Cancer Chemother. Pharmcol., 33:187–190, 1993, "Extended–release formulation of morphine for subcutaneous administration."

Ishii, Liposome Technology, 1:111–121, 1993, "Production and Size Control of large unilamellar liposomes by emulsification."

Cullis, et al., Phospholipids and Cellular Regulation, 1:65–123, 1985, "Structural properties and functional roles of phospholipids in . . . . "

Kim, et al., Cancer Chemother Pharmacology, 19:307–310, 1987, "Modulation of the peritoneal clearance of liposomal ara–C by blank liposomes."

Roy, et al., Cancer Chemother. Pharm., 28:105–108, 1991, "Multivesicular liposomes containing bleomycin for subcutaneous administration."

Kim, et al., Reg. Cancer Treat., 2:170–173, 1989, "Intratumoral chemotherapy with multivesicular liposomes containing 1–b–D–arabino . . . . "

Kim, et al., J. Inf. Dis., 162:750–752, 1990, "Multivesicular liposomes for CSF delivery of retroviral agent DDC."

Chamberlain, et al., Archives of Neurol, 50(3):261–264, 1993, Treatment of leptomeningeal metastasis with intraventricular administration of . . . .

Chatelut, et al., Cancer Them. Pharmacol., 32:179–182, 1993, "A slow–release methotrexate formulation for inratheceal chemotherapy."

Kim, et al., Biochim. Biophys. Acta, 646:1, 1981, "Preparation of cell–siz unilamellar liposomes with high captured volume and defined size . . . . "

Kim, et al., Biochim. Biophys. Acta, 728:339–348, 1983, "Preparation of multivesicular liposomes".

Kim, et al., Biochim. Biophys. Acta, 793:801, 1985, Preparation of multilamellar vesicles of defined size–distribution by solvent–spherule . . . .

Kim, et al., Cancer Treat. Rep., 71:705–711, 1987, "Multivesicular liposomes containing cytarabine entrapped in the presence of . . . . "

Kim, et al., Cancer Research, 47:3935–3937, 1987, "Multivesicular Liposomes Containing cytosine arabinoside for slow–release intrathecal therapy."

Kim, et al., Cancer Treat Rep., 71:447–450, 1987, "Multivesicular liposomes containing cytosine arabinoside for slow–release . . . . "

Bonetti, et al., Cancer Chemotherapy and Pharmacology, In Press, 1993, "An extended–release formulation of methotrexate for subcutaneous . . . . "

Kim, et al., Cancer Res., 53:1596–1598, 1993, "Prolongation of drug action in CSF by encapsulation into multivesicular liposomes."

Crommelin, Internat. J. Pharmaceutics 16, (1983) p. 79.

Freeze fracture electron micrograph of a unilamellar vesicle (ULV)

Freeze fracture electron micrograph of a multilamellar vesicle (MLV)

Freeze fracture electron micrograph of a multivesicular liposome (MVL)

MULTIVESICULAR LIPOSOMES HAVING A BIOLOGICALLY ACTIVE SUBSTANCE ENCAPSULATED THEREIN IN THE PRESENCE OF A HYDROCHLORIDE

This application is a Continuation-in-Part of U.S. Ser. No. 08/352,342, filed Dec. 7, 1994, now abandoned, which is a continuation of U.S. Ser. No. 08/020,483, filed Feb. 23, 1993, now abandoned, which is a continuation of U.S. Ser. No. 07/709,744, filed Jun. 3, 1991, now abandoned, which is continuation-in-part of U.S. Ser. No 07/563,365, filed Aug. 6, 1990, now abandoned, which is a continuation-in-part of U.S. Ser. No. 07/151,553, filed Feb. 18, 1988, now abandoned.

BACKGROUND OF THE INVENTION

1. Field of the Invention

The present invention relates to the composition of synthetic multivesicular lipid vesicles or liposomes encapsulating biologically active substances and to methods for their manufacture and use.

2. Description of Related Art

Because of the easily confused acronyms, multivesicular liposomes (MVL) have been frequently confused with multilamellar vesicles (MLV), even among those familiar with the art. Nevertheless, the two entities are entirely distinct from each other. Multivesicular liposomes (MVL) are defined as liposomes containing multiple non-concentric chambers within each liposome particle, resembling a "foam-like" matrix; whereas multilamellar liposomes (also known as multilamellar vesicles or "MLV") contain multiple concentric chambers within each liposome particle, resembling the "layers of an onion". The distinctive structural features that clearly set MVL apart from MLV are easily seen by electron microscopy (FIG. 1).

In addition to the above two types of liposomes, unilamellar liposomes (also known as unilamellar vesicles or "ULV") that enclose a single internal aqueous compartment have been described. Unilamellar liposomes include small unilamellar vesicles (SUV) (Huang, *Biochemistry* 8:334–352, 1969) and large unilamellar vesicles (LUV) (Kim et al, *Biochim. Biophys. Acta* 646:1–10, 1981). Again, the distinctive structural features that clearly set MVL apart from unilamellar liposomes are easily seen by electron microscopy (FIG. 1).

The prior art describes a number of techniques for producing unilamellar and multilamellar liposomes; for example, U.S. Pat. Nos. 4,522,803 to Lenk; 4,310,506 to Baldeschwieler; 4,235,871 to Papahadjopoulos; 4,224,179 to Schneider; 4,078,052 to Papahadjopoulos; 4,394,372 to Taylor; 4,308,166 to Marchetti; 4,485,054 to Mezei; and 4,508,703 to Redziniak. A comprehensive review of various methods for preparation of unilamellar and multilamellar liposomes can be found in Szoka et al., *Ann. Rev. Biophys. Bioeng.* 9:465–508, 1980. The prior art also describes methods for producing multivesicular liposomes (Kim, et al., *Biochim. Biophys. Acta* 728,339–348,1983). In fact, the method of Kim, et al. (*Biochim. Biophys. Acta* 728,339–348, 1983) is the only report that describes multivesicular liposomes, but the encapsulation efficiency of some of the small molecules such as cytarabine, also known as cytosine arabinoside or ara-C, was relatively low, and the release rate of encapsulated molecules in biological fluids at 37° C. could not be modulated. The prior-art multivesicular liposomes result in in vivo release of the encapsulated biologically active substance over a period less than 24 hours following a single bolus injection into a mammal and could not be modulated, which severely limits the usefulness of the prior art.

The prior art by Crommelin et al. (*Intl. J. Pharm.* 16, 79–92, 1983) discloses that multilamellar liposomes encapsulating the biologically active substance doxorubicin should be prepared in the presence of a slightly acidic medium (pH 4–6.3), because such liposomes have a slow leakage rate of doxorubicin on storage. The present invention is not intended to teach about retention or leakage of the encapsulated biologically substances on storage of vesicles as taught by Crommelin et al. As will be apparent from the Description of Preferred Embodiments, the purpose of the present invention is to teach modulation of release of the biologically active substance over time relating to its site of application in the body, as anticipated by in vitro release testing in biologically-relevant media. Furthermore, the present invention teaches that the amount of hydrochloride added during the process of multivesicular liposome preparation will modulate the subsequent release rate of the biologically active substance from the liposome at the in vivo site of application. Additionally, the present invention differs from that disclosed by Crommelin et al. (supra) because Crommelin et al. use a distinct preparation process which results in liposomes having entirely different structures from those of the multivesicular liposomes. Specifically, Crommelin et al. make multilamellar liposomes containing multiple concentric chambers within each liposome particle; whereas the present art makes multivesicular liposomes containing multiple non-concentric chambers within each liposome particle.

Optimal treatment with many drugs requires maintenance of a drug level for a prolonged period of time. For example, optimal anti-cancer treatment with cell cycle-specific anti-metabolites requires maintenance of a cytotoxic drug level for a prolonged period of time. Because it is a cell cycle phase-specific drug, cytarabine is a highly schedule-dependent anti-cancer drug. Because this drug kills cells only when they are making DNA, a prolonged exposure at therapeutic concentration of the drug is required for optimal cell kill. Unfortunately, the half-life of many drugs, including cytarabine, is very short after an intraperitoneal (IP), intravenous (IV), intrathecal (IT), intraarticular (IA), intramuscular (IM), or subcutaneous (SC) dose. To achieve optimal cancer cell kill with a cell cycle phase-specific drug like cytarabine, two major requirements need to be met: first, the cancer must be exposed to a high concentration of the drug without doing irreversible harm to the host; and second, the tumor must be exposed for a prolonged period of time so that all or most of the cancer cells have attempted to synthesize DNA in the presence of the drug.

Prior to the present invention, it has proven difficult, costly, and dangerous to provide prolonged concentration of cytarabine in the intrathecal space. The only way of achieving a prolonged cerebrospinal fluid (CSF) drug level in the case of cytarabine has been through continuous IT infusion using a drug pump. This method is not routinely employed because it carries a large risk of producing bacterial meningitis. The only way of achieving a prolonged plasma drug level in the case of cytarabine is through continuous intravenous or sub-cutaneous infusion, both of which are inconvenient and costly. In searching for a long-acting preparation, investigators in the past have attempted to achieve this by chemical modification of the drug molecule to retard metabolism or covalent attachment of a hydrophobic moiety to retard solubilization. However, such manipulations have resulted in new toxic effects (Finkelstein, et al., Cancer Treat Rep 63:1331–1333, 1979), or unacceptable pharmacokinetic or formulation problems (Ho et. al., *Cancer Res.* 37:1640–1643, 1977). Therefore, a slow-release depot preparation which provides a prolonged and sustained exposure at a therapeutic concentration of a biologically-active substance is needed. The present invention is directed to the production process, composition, and use of such a preparation.

A BRIEF DESCRIPTION OF THE DRAWING

FIGS. 1A, B and C show respectively, illustrative electron micrographs of unilamellar vesicles (ULV), which contain a single internal aqueous compartment and usually have a diameter of 0.02–0.5 micrometers; multilamellar vesicles (MLV), which contain multiple concentric internal aqueous compartments and usually have a diameter of 0.2–5 micrometers; and multivesicular liposomes (MVL), which contain multiple non-concentric internal aqueous compartments and usually have a diameter of 1–100 micrometers.

SUMMARY OF THE INVENTION

The present invention provides a multivesicular liposome containing a biologically active substance encapsulated in the presence of a hydrochloride, which is used to effectively modulate the release rate of the encapsulated biologically active substance. The multivesicular liposome system can be used to provide prolonged and sustained in vivo exposure at a disease site of a therapeutic concentration of the biologically active substance for optimal results. The present invention also provides methods for making such multivesicular liposomes.

The multivesicular liposomes of this invention provide high encapsulation efficiency; controlled release rate of the encapsulated substance; well defined, reproducible size distribution among the liposomes; adjustable average size that can be easily controlled; and adjustable internal chamber size and number.

The process for producing the multivesicular lipid vesicles or liposomes comprises: (a) dissolving in one or more organic solvents a lipid component containing at least one neutral lipid and at least one amphipathic lipid; (b) adding into the lipid component an immiscible first aqueous component containing one or more biologically active substances to be encapsulated; (c) adding a hydrochloride to either or both the first aqueous component and the lipid component, forming a water-in-oil emulsion from the two immiscible components; d) dispersing the water-in-oil emulsion with a second aqueous component to form solvent spherules containing in them multiple droplets of the first aqueous component, and (e) removing the organic solvents, such as by evaporation, from the solvent spherules to form the multivesicular liposomes. According to the present invention, the addition of a hydrochloride, such as hydrochloric acid or other hydrochlorides such as lysine hydrochloride, is essential for high encapsulation efficiency and controlled release rate of encapsulated molecules in biological fluids and in vivo.

Accordingly, it is an object of the present invention to provide a depot preparation which can be used to provide controlled-release of a biologically active substance at a therapeutic concentration to an in vivo site.

A further object of the present invention is to provide a multivesicular liposome which can be used to provide controlled-release of a biologically active substance at a therapeutic concentration to an in vivo site.

A further object of the present invention is the provision of a multivesicular liposome encapsulating a biologically active substance in the presence of a hydrochloride which can effectively modulate the release rate of the encapsulated biologically active substances, and can be used to provide a controlled, prolonged and sustained exposure of the biologically active substance at a therapeutic concentration for optimal results.

It is a further object of the present invention to provide a method for preparing such a depot preparation. Other and further objects, features, and advantages of the invention are inherent herein and appear throughout the specifications and claims.

DESCRIPTION OF PREFERRED EMBODIMENTS

Figure 1A:
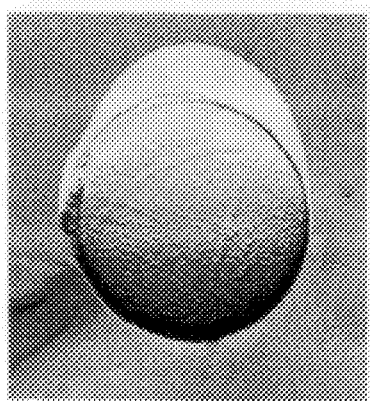
Figure 1B:
Figure 1C:
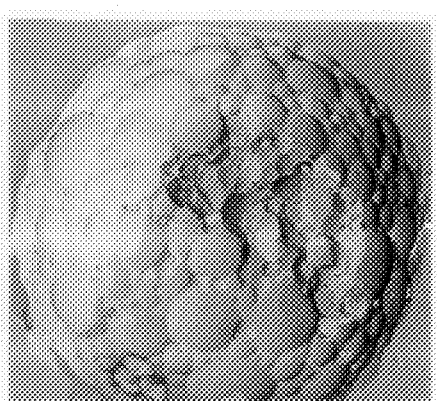

The term "multivesicular liposomes" as used throughout the specifications and claims means man-made, microscopic lipid vesicles consisting of lipid bilayer membranes, enclosing multiple non-concentric aqueous chambers, resembling a "foam-like" matrix. In contrast, unilamellar liposomes have a single aqueous chamber; and multilamellar liposomes have a multiple "onion-skin" arrangement of concentric membranes, in between which are aqueous compartments.

The term "solvent spherule" as used throughout the specifications and claims means a microscopic spheroid droplet of organic solvent, within which are multiple smaller droplets of aqueous solution. The solvent spherules are suspended and totally immersed in a second aqueous solution.

The term "neutral lipid" as used herein means oil or fats that have no membrane-forming capability by themselves and lack a hydrophilic "head" group.

The term "amphipathic lipid" as used herein means a lipid that has a hydrophilic "head" group and a hydrophobic "tail" group, and has membrane-forming capability.

The term "anionic amphipathic lipid" as used herein means an amphipathic lipid that carries a net negative charge at pH 7.4.

The term "zwitterionic amphipathic lipid" as used herein means an amphipathic lipid that carries no net charge at pH 7.4.

The term "cationic amphipathic lipid" as used herein means an amphipathic lipid that carries a net positive charge at pH 7.4.

The term "hydrohalic acid" as used herein means a compound selected from the group consisting of hydrochloric acid, hydrofluoric acid, hydrobromic acid, or hydroiodic acid.

The term "hydrochloride" as used herein means hydrochloric acid or a hydrochloric acid salt of an organic base, or a combination thereof.

The term "hydrohalide" as used herein means a hydrohalic acid or hydrohalic acid salt of an organic base, or a combination thereof.

The term "modulate the release" as used herein means to increase or decrease the release rate, or otherwise to alter the release pattern of encapsulated biologically active substances from multivesicular liposomes.

The term "biologically active substance" as used herein means a chemical compound that is known in the art as having utility for modulating biological processes so as to achieve a desired effect in modulation or treatment of an undesired existing condition in a living being, such as a medical, agricultural or cosmetic effect. Thus, biologically active substances are generally selected from the broad categories of medicaments, agricultural products and cosmetics. Representative biologically active substances are disclosed in Table 1 below.

The multivesicular liposomes of the invention are made by the following process, which process imparts to them their characteristic properties, including the properties of modulated release of encapsulated biologically active substances disclosed herein. Briefly, a "water-in-oil" emulsion containing the biologically active substance to be encapsulated is first made by dissolving the amphipathic lipids and the neutral lipids in a volatile organic solvent for the lipid component, adding to the lipid component an immiscible first aqueous component and adding a hydrochloride to either or both of the first aqueous component and the lipid component, and then emulsifying the mixture, for example, mechanically as by mixing, shaking, sonication, by ultrasonic energy, nozzle atomization, or combinations thereof. The biologically active substance to be encapsulated can be contained in the first aqueous component or the lipid component, or both. The whole water-in-oil emulsion is then mixed with the second aqueous component and then agitated mechanically, as above, to form solvent spherules suspended in the second aqueous component. The solvent spherules contain multiple aqueous droplets with the substance to be encapsulated dissolved therein.

The volatile organic solvent is removed, for instance by evaporation, from the spherules. When the solvent is completely evaporated, multivesicular liposomes are formed. Representative gases satisfactory for use in evaporating the solvent include nitrogen, helium, argon, oxygen, hydrogen and carbon dioxide. Alternatively, the organic solvent can be removed by sparging, rotary evaporation, or solvent selective membranes.

According to the present invention, the addition of sufficient hydrochloride effective for high encapsulation efficiency and for controlled release rate of encapsulated biologically active substances in biological fluids and in vivo is essential. Hydrochloric acid is the preferred hydrochloride, but other hydrochlorides which are satisfactory include, but are not limited to, lysine hydrochloride, histidine hydrochloride, arginine hydrochloride, triethanolamine hydrochloride, pyridine hydrochloride, and combinations thereof. Also, other hydrohalic acids, such as hydrochloric acid, hydrofluoric acid, hydrobromic acid, and hydroiodic acid, may be used. In the practice of this invention, modulation of release rate of the encapsulated biologically active substance is achieved by adjusting the concentration of hydrochloride present in either the lipid component or in the first aqueous component used to form the water-in-oil emulsion during formation of the multivesicular liposomes to arrive at the desired release rate, i.e., a therapeutically effective release rate of a medicament or other biologically active substance. It should be noted that, depending upon the concentration of hydrochloride used, the release rate of the biologically active substance from the multivesicular liposomes can either be increased or decreased over that achieved when the hydrochloride is not used in manufacture of the liposomes.

As one of skill in the art will appreciate, the amount of hydrochloride used with any particular multivesicular liposome composition containing a biologically active substance will depend upon the chemical properties of the liposome (i.e., the combination of lipids used in its formulation), the aqueous solution encapsulated in the liposome, the environment into which the liposome is to be placed (i.e., physiological saline or tissue implant); as well as upon those of the biologically active substance. Using the guidelines provided herein and illustrated in the Examples hereafter, one skilled in the art can readily use routine experimentation to arrive at the amount of the hydrochloride to be used during manufacture of the multivesicular liposome to either increase or decrease the rate of release of the biologically active substance. For instance, as illustrated in Example 2, when the first aqueous solution contains 20 mg/ml of cytarabine, addition of hydrochloric acid in the range from about 10 to 70 mM during manufacture of the liposomes results in an increase in the rate of release of cytarabine; whereas addition of hydrochloric acid in the range from about 70 to 500 mM results in a decrease in the rate of release of the drug as compared with liposomes free of hydrochloric acid during their manufacture.

Generally, the hydrochloride and the biologically active substance are added to the first aqueous solution if the drug or other biologically active substance to be encapsulated is hydrophilic. On the other hand, if the biologically active substance is lipophilic, it is preferred to add the hydrochloride and the biologically active component to the lipid component to be used in formation of the water-in-oil emulsion. One skilled in the art will know how to select the most appropriate hydrochlorides for incorporation into either aqueous or lipid components.

Many different types of volatile hydrophobic solvents, such as ethers, halogenated ethers, hydrocarbons, esters, halogenated hydrocarbons, or Freons may be used as the lipid-phase solvent. For example, diethyl ether, isopropyl and other ethers, chloroform, tetrahydrofuran, ethyl acetate, Forane, and combinations thereof, are satisfactory for use in making the multivesicular liposomes of this invention.

Various types of lipids can be used to make multivesicular liposomes, and the only two minimum requirements regarding the lipids are that the lipid component contain one neutral lipid and one amphipathic lipid. Examples of neutral lipids include diglycerides, such as diolein, dipalmitolein; propylene glycol esters such as mixed diesters of caprylic/capric acids on propylene glycol; triglycerides such as triolein, tripalmitolein, trilinolein, tricaprylin, and trilaurin; squalene; and combinations thereof. Examples of amphipathic lipids include those with net negative charge, zero net charge, and net positive charge at pH 7.4, such as phosphatidylglycerol (PG), cardiolipin (CL), phosphatidylserine (PS), phosphatidic acid (PA), phosphatidylinositol, phosphatidylcholine (PC), phosphatidylethanolamine (PE), sphingomyelin, diacyl trimethylammoniumpropane (DITAP), and various combinations thereof. Some examples of lipid combinations used to make multivesicular liposomes include, PC/cholesterol/CL/triolein in 4.5/4.5/1/1 molar ratio; PC/cholesterol/PS/triolein in 4.5/4.5/1/1 molar ratio; PC/cholesterol/PG/triolein in 5/4/1/1 molar ratio; PC/phytosterol/PG/triolein in 5/4/1/1 molar ratio; PC/cholesterol/PG/tripalmitolein in 4/5/1/1 molar ratio; PG/triolein in 9/1 molar ratio; PC/cholesterol/PE/triolein in 4/5/1/1 molar ratio; PE/cholesterol/CL/triolein in 4.5/4.5/1/1 molar ratio; PC/cholesterol/PA/triolein in 4.5/4.5/1/1 molar ratio; and PC/cholesterol/DITAP/triolein in 4/5/1/1 molar ratio.

Many and varied biologically active substances can be incorporated by encapsulation within the multivesicular liposomes. These include small molecule drugs, nucleic acids such as DNA and RNA, proteins of various types including hormones produced by recombinant DNA technology, hematopoietic growth factors, monokines, lymphokines, tumor necrosis factor, inhibin, tumor growth factor alpha and beta, cytokines, interferons, Mullerian inhibitory substance, nerve growth factor, fibroblast growth factor, platelet-derived growth factor, pituitary and hypophyseal hormones including leutenizing hormone and other releasing hormones, calcitonin, and proteins that serve as immunogens for vaccination.

Table 1 includes representative classes of biologically active substances which can be encapsulated in multivesicular liposomes in the presence of a hydrochloride and which are effective in humans, and includes biologically active substances effective for agricultural uses.

TABLE 1

| Anesthetics | Antianginas | Antiarrhythmics |
| Antiasthmatic Agents | Antibiotics | Antidiabetics |
| Antifungals | Antihistamines | Antihypertensives |
| Antiparasitics | Antineoplastics | Antivirals |
| Cardiac Glycosides | Herbicides | Hormones |
| Immunomodulators | Monoclonal Antibodies | Neurotransmitters |
| Nucleic Acids | Peptides | Pesticides |
| Proteins | Radio contrasts | Radionuclides |
| Sedatives and Analgesics | Steroids | Tranquilizers |
| Vaccines | Vasopressors | |

Particularly preferred biologically active substances for use in the practice of this invention are cytarabine, morphine, hydromorphone, leuprolide, interleukin-2, amikacin, granulocyte colony stimulating factor, insulin, hepatitis B vaccine, granulocyte-macrophage colony stimulating factor, methotrexate, insulin-like Growth Factor—1, and α-interferon.

The present invention additionally provides a method of treating a pathophysiological state in an individual comprising administering a liposome composition of this invention to the individual, said composition comprising a biologically active substance encapsulated in said liposome, which biologically active compound is released from the liposome at a therapeutically effective dosage rate. The term "therapeutically effective" as it pertains to the compositions of the invention means that the biologically active therapeutic substance within the vesicles is released therefrom at a concentration and rate sufficient to achieve a particular medical effect for which the therapeutic substance is intended. Examples, without limitation, of desirable medical effects that can be attained are chemotherapy, antibiotic therapy, and regulation of metabolism. Exact dosages will vary depending upon such factors as the particular biologically active or therapeutic substance and desirable medical effect, as well as patient factors such as age, sex, general condition, and the like. Those of skill in the art can readily take these factors into account and use them to establish effective therapeutic concentrations without resort to undue experimentation.

Generally, however, the range of dosages of a therapeutic agent appropriate for human use in the practice of this invention includes the range of 0.1–6000 mg/sq m of bodily surface area. The reason that this range is so large is that for some applications, such as subcutaneous administration, the dose required may be quite small, but for other applications, such as intraperitoneal administration, the dose desired to be used may be enormous. While doses outside the foregoing dose range may be given, this range encompasses the breadth of use for most biologically active substances.

Multivesicular liposomes may be administered by any desired route; for example, by intratumoral, intramuscular, intrathecal, intraperitoneal, subcutaneous, intravenous, intralymphatic, intraarticular, oral and submucosal administration, as well as by implantation (i.e., surgically) under many different kinds of epithelia, including the bronchiolar epithelia, the gastrointestinal epithelia, the urogenital epithelia, and various mucous membranes of the body.

The following examples illustrate the manner in which the invention can be practiced. It is understood, however, that the examples are for the purpose of illustration and the invention is not to be regarded as limited to any of the specific materials and conditions therein.

EXAMPLE 1

This example illustrates a preparation of multivesicular liposomes and the advantage of using a hydrochloride to modulate the release rate of the encapsulated biologically active substances, as compared to the prior art multivesicular liposomes made in the absence of a hydrochloride.

A. Preparation of multivesicular liposomes encapsulating biologically active substance in the presence of a hydrochloride Step 1) In a clean one-dram glass vial (1.3 cm inner diameter×4.5 cm height), were placed 1 ml of a chloroform solution containing 9.3 μmoles of dioleoyl phosphatidylcholine (Avanti Polar Lipids, Alabaster, Ala.), 2.1 μmoles of dipalmitoyl phosphatidylglycerol (Avanti Polar Lipids), 15 μmoles of cholesterol (Sigma Chemical Co., St. Louis, Mo.), 1.8 μmoles of triolein (Avanti Polar Lipids). This solution is referred to as the lipid component.

Step 2) One ml of an aqueous solution containing 20 mg/ml of cytarabine (Upjohn, Kalamazoo, Mich.) and 136 mM of hydrochloric acid, was added into the above one-dram glass vial containing the lipid component.

Step 3) For making the water-in-oil emulsion, the glass vial containing the mixture of "Step 2" was sealed and attached to the head of a vortex shaker (American Scientific Products, Catalogue, McGaw Park, Ill.) and shaken at setting "10" for 6 minutes.

Step 4) For making the chloroform spherules suspended in water, the water-in-oil emulsion obtained from "Step 3" was divided in equal volume into two one-dram glass vials (1.3 cm inner diameter×4.5 cm height), each containing 2.5 ml of 4 percent glucose and 40 mM lysine in water; each vial was then sealed, attached to the head of the same vortex shaker as used in "Step 3" and shaken at setting "5" for 3 seconds.

Step 5) To obtain the multivesicular liposomes, chloroform spherule suspensions produced in the two vials of "Step 4" were poured into the bottom of a 250 ml Erlenmeyer flask containing 5 ml of 3.5 g/100 ml glucose and 40 mM lysine in water. With the flask kept in 37° C. shaking water bath, a stream of nitrogen gas at 7 L/minute was flushed through the flask to slowly evaporate chloroform over 10–15 minutes. The liposomes were then isolated by centrifugation at 600×g for 5 minutes; the supernatant was decanted, and the liposome pellet was resuspended in 5 ml of normal saline (0.9% sodium chloride). The liposomes were isolated again by centrifugation at 600×g for 5 minutes. The supernatant was decanted and the pellet was resuspended in normal saline.

B. Characterization of multivesicular liposomes

The mean volume-weighted diameter±standard deviation of the multivesicular liposomes obtained as described above was typically 19.4±6.5 μm. The percent encapsulation of cytarabine was typically 59±7 percent and the encapsulated volume typically 36±4 μl/mg of total lipids used.

C. Preparation of multivesicular liposomes encapsulating a biologically active substance in the absence of a hydrochloride as a control for comparison Multivesicular liposomes encapsulating cytarabine in the absence of hydrochloride were prepared according to the same procedure as described in Part A above except that no hydrochloric acid was used in "Step 2".

D. In Vitro and In Vivo Assays for Cytarabine Release from Multivesicular Liposomes In Vitro assay: To a pellet of the centrifuged multivesicular liposome containing cytarabine, at least 100-fold volume of blood bank human plasma containing 0.01% sodium azide was added. The liposome suspension was placed in a syringe and air was excluded from the syringe. The syringe was placed on a rotary shaker (G10 Gyrotory Shaker, New Brunswick Scientific Co. New Brunswick, N.J.) and incubated while being shaken at 37° C. At desired time points, an aliquot was removed from the syringe, diluted with normal saline, and the multivesicular liposomes were isolated as a pellet by centrifugation. The amount of cytarabine in multivesicular liposomes was measured by either spectrophotometric method or by the method of HPLC. The percent retained cytarabine at each time point was calculated in reference to the drug amount at time zero and a half-life was estimated assuming a single-exponential decay model.

In Vivo assay: Mice were injected intraperitoneally (IP) with 1 ml of the multivesicular liposome suspension containing cytarabine. At desired time points, 2 to 3 animals were sacrificed by cervical dislocation. The peritoneal cavity was washed out thoroughly with 10 ml of normal saline. All samples were stored at −20° C. before analysis. The samples were analyzed for cytarabine by HPLC. The percent retained cytarabine in vivo at each time point was calculated in reference to the drug amount at time zero and a half-life might be estimated assuming a single-exponential decay model.

Tables 2 shows some representative data obtained from in vitro cytarabine release assay for multivesicular liposomes encapsulating cytarabine in the presence and absence of hydrochloric acid. These data demonstrate that addition of hydrochloric acid can greatly decrease the rate of cytarabine release out of the multivesicular liposomes. For instance, percent retained cytarabine at 24 hour was 93% when hydrochloric acid was used, in contrast to 52% when hydrochloric acid was not used.

TABLE 2

In Vitro Release of Cytarabine

| Hours of Incubation in Plasma at 37° C. | Percent Retained With 136 mM Hcl | Cytarabine Without HCl |
| --- | --- | --- |
| 0 | 100 | 100 |
| 24 | 93 | 52 |
| 96 | 78 | 19 |
| 192 | 57 | — |
| 336 | 47 | — |

EXAMPLE 2

This example demonstrates that the release rate of the encapsulated biologically active substance from multivesicular liposomes can be effectively modulated by varying the concentration of hydrochloric acid used.

The same procedure as described in Step 1 through Step 5 of Example 1 was used for the preparation of multivesicular liposomes except with the following modifications in Step 2.

Step 2) One ml of an aqueous solution containing 20 mg/ml of cytarabine (Upjohn, Kalamazoo, Mich.) and 10 to 500 mM of hydrochloric acid, was added into the above one-dram glass vial containing the lipid component.

Table 3 shows a summary of data obtained from in vitro cytarabine release assay for multivesicular liposomes encapsulating cytarabine in the presence of various concentrations of hydrochloric acid. These data demonstrate the release rate from the multivesicular liposomes can either be increased or decreased depending on the specific concentration of hydrochloric acid used. For instance, when the biologically active substance is encapsulated in the presence of hydrochloric acid in the range of 10 to 70 mM, the release rate is increased, but when the biologically active substance is encapsulted in the presence of hydrochloric acid in a different concentration range, i.e. in the range of 70 to 500 mM hydrochloric acid, the release rate is decreased. In other words, a method of modulating the release rate of the biologically active substance by adjusting the hydrochloric acid concentration has been found.

TABLE 3

In Vitro Release of Cytarabine

| Hours in Plasma | Percent Retained Cytarabine at Different HCl Concentration | | | | | |
| --- | --- | --- | --- | --- | --- | --- |
| | 0 mM | 10 mM | 20 mM | 40 mM | 70 mM | 80 mM |
| 0 | 100 | 100 | 100 | 100 | 100 | 100 |
| 24 | 59 | 52 | 39 | 34 | 15 | 25 |
| 48 | 52 | 44 | 39 | 35 | 20 | |

| Hours in Plasma | Percent Retained Cytarabine at Different HCl Concentration | | | | | |
| --- | --- | --- | --- | --- | --- | --- |
| | 90 mM | 100 mM | 200 mM | 300 mM | 400 mM | 500 mM |
| 0 | 100 | 100 | 100 | 100 | 100 | 100 |
| 24 | 68 | 86 | 83 | 86 | 62 | 68 |
| 48 | | 65 | 74 | 82 | 54 | 78 |

Similarly, the in vivo release rate of cytarabine can also be modulated by encapsulating the biologically active substance into the multivesicular liposomes in the presence of hydrochloric acid, as shown in Table 4. These latter data demonstrate that hydrochloric acid can be used to effectively reduce the release rate of cytarabine in vivo. For instance, addition of 100 to 400 mM of hydrochloric acid in "Step 2" during manufacture of the liposomes, as described above, resulted in a significant increase of percent retained cytarabine at 7 and 28 hour time points.

TABLE 4

In Vivo Release of Cytarabine

| Hours after Injection in Mice | Percent Retained Cytarabine at different HCl Concentration | | | |
| --- | --- | --- | --- | --- |
| | 0 mM | 70 mM | 80 mM | 90 mM |
| 0 | 100 | 100 | 100 | 100 |
| 7 | 2 | 1 | 5 | 13 |
| 28 | 0 | 0 | 0 | 0 |

| Hours after Injection in Mice | Percent Retained Cytarabine at different HCl Concentration | | | |
| --- | --- | --- | --- | --- |
| | 100 mM | 200 mM | 300 mM | 400 mM |
| 0 | 100 | 100 | 100 | 100 |
| 7 | 30 | 33 | 59 | 35 |
| 28 | 18 | 25 | 38 | 7 |

EXAMPLE 3

This example demonstrates that the release rate of morphine from multivesicular liposomes can be modulated by varying the concentration of hydrochloric acid present during encapsulation of the drug into the multivesicular liposomes.

The same procedure as described in Step 1 through Step 5 of Example 1 was used for the preparation of multivesicular liposomes except with the following modifications in Step 2.

Step 2) One ml of an aqueous solution containing 20 mg/ml of morphine sulfate (Sigma, St. Louis, Mo.) and 0 to 300 mM of hydrochloric acid, was added into the above one-dram glass vial containing the lipid component.

Table 5 shows that the release of encapsulated morphine in vitro can be modulated by varying the concentration of hydrochloric acid used in the preparation of multivesicular liposomes. For instance, a decreased release rate of morphine was observed with an increased concentration of hydrochloric acid in the range of 0 to 200 mM.

TABLE 5

In Vitro Release of Morphine

| Hours in Plasma | Percent Retained Morphine at different HCl Concentration | | | | | |
|---|---|---|---|---|---|---|
| | 0 mM | 25 mM | 50 mM | 100 mM | 200 mM | 300 mM |
| 0 | 100 | 100 | 100 | 100 | 100 | 100 |
| 24 | — | 55 | — | — | 100 | 100 |
| 48 | 45 | — | 52 | 69 | — | — |
| 72 | — | 28 | — | — | 99 | 99 |
| 96 | 15 | — | 31 | 57 | — | — |

EXAMPLE 4

This example demonstrates that the release rate of iohexol from multivesicular liposomes can be modulated by varying the concentration of hydrochloric acid.

The same procedure as described in Step 1 through Step 5 of Example 1 was used for the preparation of multivesicular liposomes except with the following modifications in Step 2.

Step 2) One ml of an aqueous solution containing 20 mg/ml of iohexol (Sanofi, New York, N.Y.) and 0 to 400 mM of hydrochloric acid, was added into the above one-dram glass vial containing the lipid component.

Table 6 shows that the release rate of encapsulated iohexol in vitro can be modulated by varying the concentration of hydrochloric acid used in the preparation of multivesicular liposomes, similar to what was found in the cases of cytarabine and morphine in examples 1–3 above. For instance, a slower in vitro release rate of iohexol was observed with an increased concentration of hydrochloric acid in the range of 0 to 100 mM. A further increase of hydrochloric acid concentration from 100 to 400 mM resulted in a faster release rate of iohexol.

TABLE 6

In Vitro Release of Iohexol

| Hours in Plasma | Percent Retained Iohexol at different HCl Concentration | | | | |
|---|---|---|---|---|---|
| | 0 mM | 50 mM | 100 mM | 200 mM | 400 mM |
| 0 | 100 | 100 | 100 | 100 | 100 |
| 24 | 50 | 105 | 103 | 68 | 57 |
| 48 | 54 | 82 | 86 | 57 | 55 |

EXAMPLE 5

This example illustrates a different procedure and a larger scale for the preparation of multivesicular liposomes, but shows the similar effects of a hydrochloride in modulating the release of encapsulated biologically active substances as described in Examples 1 through 4 above.

Step 1) Into a clean glass cylinder (2.5 cm inner diameter× 10.0 cm height) were placed 5 ml of a chloroform solution containing 46.5 μmoles of dioleoyl phosphatidylcholine (Avanti Polar Lipids), 10.5 μmoles of dipalmitoyl phosphatidylglycerol (Avanti Polar Lipids), 75 μmoles of cholesterol (Sigma Chemical Co.), 9.0 μmoles of triolein (Avanti Polar Lipids). This solution is referred to as the lipid component.

Step 2) Five ml of an aqueous solution containing 20 mg/ml of cytarabine (Upjohn, Kalamazoo, Mich.) and 136 mM of hydrochloric acid, was added into the above glass cylinder containing the lipid component.

Step 3) For making the water-in-oil emulsion, the mixture of "Step 2" was stirred with a TK mixer (AutoHomoMixer, Model M, Tokushu Kika, Osaka, Japan) at a speed of 9000 revolution per minute (rpm) for 8 minutes.

Step 4) For making the chloroform spherules suspended in water, 20 ml of a solution containing 4 percent glucose and 40 mM lysine in water was layered on top of the water-in-oil emulsion of "Step 3" and then mixed at a speed of 4000 rpm for 60 seconds.

Step 5) To obtain the multivesicular liposomes, the chloroform spherule suspension in the glass cylinder was poured into the bottom of a 1000 ml Erlenmeyer flask, containing 30 ml of 4 percent glucose and 40 mM lysine in water. With the container kept in 37° C. shaking water bath, a stream of nitrogen gas at 7 L/minute was flushed through the flask to slowly evaporate chloroform over 20 minutes. The liposomes were then isolated by centrifugation at 600×g for 5 minutes; the supernatant was decanted, and the liposome pellet was resuspended in 5 ml of normal saline. The liposomes were isolated again by centrifugation at 600×g for 5 minutes. The supernatant was decanted and the pellet was resuspended in normal saline.

EXAMPLE 6

This example demonstrates that the addition of a hydrochloride other than hydrochloric acid, such as arginine hydrochloride, histidine hydrochloride, lysine hydrochloride, pyridine hydrochloride, or triethanolamine hydrochloride, in the preparation of multivesicular liposomes, is also effective in modulating the release rate of liposome encapsulated cytarabine.

The same procedure as described in Step 1 through Step 5 of Example 1 was used for the preparation of multivesicular liposomes except with the following modifications in Step 1 and Step 2.

Step 1) Into a clean one-dram glass vial (1.3 cm inner diameter×4.5 cm height), were placed 1 ml of a chloroform solution containing 13 μmoles of dioleoyl phosphatidylcholine (Avanti Polar Lipids), 2.9 μmoles of dipalmitoyl phosphatidylglycerol (Avanti Polar Lipids), 20 μmoles of cholesterol (Sigma Chemical Co.), 2.5 μmoles of triolein (Avanti Polar Lipids). This solution is referred to as the lipid component.

Step 2) One ml of an aqueous solution containing 2 mg/ml of cytarabine (Upjohn, Kalamazoo, Mich.) and 100 mM of either arginine hydrochloride, or histidine hydrochloride, or lysine hydrochloride, or pyridine hydrochloride, or triethanolamine hydrochloride, was added into the above one-dram glass vial containing the lipid component.

Table 7 shows in vitro release data for cytarabine encapsulated in multivesicular liposomes in the presence of either arginine hydrochloride, or histidine hydrochloride, or lysine hydrochloride, or pyridine hydrochloride, or triethanolamine hydrochloride, assayed according to the same procedure as described in Part D of Example 1. These data demonstrate that the addition of a hydrochloric acid salt of an organic base during encapsulation of the biologically active substance into the liposomes can also modulate the release rate of cytarabine from the multivesicular liposomes incubated in plasma. For instance, the percent retained cytarabine at 24 hours was 95%, 91%, 97%, 97%, and 62%, respectively, when arginine hydrochloride, histidine hydrochloride, lysine hydrochloride, pyridine hydrochloride, and triethanolamine hydrochloride were used; whereas the percent retained cytarabine at 24 hours was 50% when the hydrochloride was omitted, and replaced with 4 percent glucose in Step 2 of the manufacturing process disclosed above.

TABLE 7

In Vitro Release of Cytarabine

| | Percent Retained Cytarabine | |
|---|---|---|
| Hydrochloride | At 24 hours | At 72 hours |
| Arginine HCl | 95 | 117 |
| Histidine HCl | 91 | 38 |
| Lysine HCl | 97 | 69 |
| Pyridine HCl | 97 | 97 |
| Triethanolamine HCl | 62 | 33 |
| No Hydrochloride | 50 | 10 |

EXAMPLE 7

This example demonstrates that proteins can be encapsulated in multivesicular liposomes and that a hydrochloride introduced during the encapsulation of the protein into the liposomes is effective in modulating the release of encapsulated proteins.

The same procedure as described in Step 1 through Step 5 of Example 1 was used for the preparation of multivesicular liposomes except with the following modifications in Step 2.

Step 2) One ml of an aqueous solution containing 0.3 mg/ml of the protein, granulocyte colony stimulating factor (G-CSF), (Neupogen®, Amgen Corporation, Thousand Oaks, Calif.), 175 mM glycine, and 100 mM of hydrochloric acid was added into the above one-dram glass vial containing the lipid component.

Table 5 shows in vitro release data for G-CSF encapsulated in multivesicular liposomes in the presence and absence of 100 mM of hydrochloric acid, assayed according to the same procedure as described in Part D of Example 1 except that the quantity of G-CSF was determined by an HPLC method. These data demonstrate that addition of 100 mM hydrochloric acid reduced the release rate of G-CSF from the multivesicular liposomes when incubated in plasma. For instance, the percent retained G-CSF at 13 and 37 hours was 51% and 24%, respectively, when 100 mM of hydrochloric acid was used; whereas the percent retained G-CSF at 13 and 37 hours was 24% and 3%, respectively, when hydrochloric acid was omitted.

TABLE 8

In Vitro Release of G-CSF

| Hours of Incubation in Plasma at 37° C. | Percent Retained With 100 mM Hcl | G-CSF Without HCl |
|---|---|---|
| 0 | 100 | 100 |
| 13 | 51 | 24 |
| 37 | 29 | 3 |
| 84 | 16 | 0 |

EXAMPLE 8

This example demonstrates that nucleic acids, such as DNA, can be encapsulated in multivesicular liposomes and that a hydrochloride is effective in modulating the release of encapsulated nucleic acids.

The same procedure as described in Step 1 through Step 5 of Example 1 was used for the preparation of multivesicular liposomes except with the following modifications in Step 2.

Step 2) One ml of an aqueous solution containing 5 mg/ml of Herring sperm DNA (Sigma Chemical Co.) and 100 mM of lysine hydrochloride was added into the above one-dram glass vial containing the lipid component.

Table 6 shows in vitro release data for Herring sperm DNA encapsulated in multivesicular liposomes in the presence and absence of 100 mM of lysine hydrochloride, assayed according to the same procedure as described in Part D of Example 1. These data demonstrate that addition of 100 mM lysine hydrochloride reduced the release rate of Herring sperm DNA from the multivesicular liposomes when incubated in plasma. For instance, the percent retained Herring sperm DNA at 24 and 120 hours was 95% and 81%. respectively, when 100 mM of lysine hydrochloride was used; whereas the percent retained Herring sperm DNA was 83% and 39%, respectively, when 100 mM of lysine hydrochloride was omitted.

TABLE 9

In Vitro Release of Herring Sperm DNA

| Hours of Incubation | Percent Retained DNA | |
|---|---|---|
| in Plasma at 37° C. | With 100 mM Lysine HCl | Without Lysine HCl |
| 0 | 100 | 100 |
| 24 | 95 | 83 |
| 72 | 95 | 40 |
| 120 | 81 | 39 |
| 192 | 80 | 38 |

Thus, the present invention provides methods with wide applications and uses for "depot" preparations in which biologically active substances can be encapsulated in relatively large amounts and released at desired rates as modulated by adjusting the hydrochloride concentration present during the procedure used to encapsulate the biologically active substance. Further, the methods of this invention allow for delivery at therapeutically effective concentrations of biologically active substances for optimal results while avoiding high peaking of dosage, which could often be toxic. The present invention is, therefore, well suited and adapted to achieve the objects as set forth in the invention and has the advantages and features mentioned as well as others inherent therein.

While presently preferred embodiments of the invention have been given for the purpose of disclosure, changes may be made therein which are within the spirit of the invention as defined by the scope of the appended claims.

What is claimed is:

1. A process for producing a multivesicular liposome having multiple non-concentric chambers with membranes distributed in a matrix, the process comprising the steps of:
   (a) forming a water-in-oil emulsion from two immiscible components, the two immiscible components being (1) a lipid component comprising at least one organic solvent, at least one amphipathic lipid, and a neutral lipid lacking a hydrophilic head group, and (2) a first aqueous component; said water-in-oil emulsion further comprising a hydrochloride selected from the group consisting of hydrochloric acid, arginine hydrochloride, histidine hydrochloride, lysine hydrochloride and pyridine hydrochloride, and combinations thereof, in a concentration in the range from about 10 mM to about 500 mM and at least one biologically active substance selected from the group consisting of an anesthetic, an antiasthmatic agent, a cardiac glycoside, an antihypertensive, a nucleic acid, an antibiotic, a vaccine, an antiarrhythmic, an antiangina, a hormone, an antidiabetic, at antineoplastic, an immunomodulator, an antifungal, a tranquilizer, a steroid, a sedative, an analgesic, a vasopressor, an antiviral, a herbicide, a pesticide, a protein, a peptide, a neurotransmitter, a radionuclide, and suitable combinations thereof, said hydrochloride and biologically active agent being independently incorporated into either the lipid component or the first aqueous component, or into both;
   (b) dispersing the water-in-oil emulsion containing the hydrohalide into a second aqueous component to form solvent spherules; and thereafter
   (c) removing the organic solvent from the solvent spherules to form the multivesicular liposomes suspended in the second aqueous component;
   wherein the hydrohalide concentration in the water-in-oil emulsion is chosen to modulate the in vivo release rate of the biologically active substance.

2. The process of claim 1 wherein, the hydrohalide is hydrochloric acid.

3. The process of claim 1 wherein, the hydrochloride is chosen from the group consisting of lysine hydrochloride, histidine hydrochloride, arginine hydrochloride, and combinations thereof.

4. The process of claim 1 wherein, the amphipathic lipid comprises at least one zwitterionic amphipathic lipid.

5. The process of claim 1 wherein, the amphipathic lipid comprises at least one cationic amphipathic lipid.

6. The process of claim 1 wherein, the amphipathic lipid comprises at least one anionic amphipathic lipid.

7. The process of claim 1 wherein, the amphipathic lipid comprises at least one zwitterionic and at least one cationic amphipathic lipid.

8. The process of claim 1 wherein, the amphipathic lipid comprises at least one zwitterionic and at least one anionic amphipathic lipid.

9. The process according to claim 4, 5, 6, 7, or 8 wherein, the amphipathic lipid is selected from the group consisting of phospholipids.

10. The process according to claim 9 wherein, the phospholipids are selected from the group consisting of phosphatidylcholine, cardiolipin, phosphatidylethanolamine, sphingomyelin, lysophosphatidylcholine, phosphatidylserine, phosphatidylinositol, phosphatidylglycerol, and phosphatidic acid.

11. The process according to claim 1 or 2 wherein, the lipid component further comprises.

12. The process according to claim 1 or 2 wherein, the lipid component further comprises stearylamine, or diacyl dimethylammoniumpropane, or diacyl trimethylammoniumpropane.

13. The process according to claim 1 or 2 wherein, the biologically active substance is lipophilic and is incorporated into the lipid component.

14. The process according to claims 4, 5, 6, 7, or 8 wherein, the neutral lipid is a triglyceride.

15. The process according to claims 4, 5, 6, 7, or 8 wherein, the neutral lipid is a diglyceride.

16. The process according to claims 4, 5, 6, 7, or 8 wherein, the neutral lipid is a propylene glycol ester.

17. The process according to claim 14 wherein, the triglyceride is selected from the group consisting of triolein, tripalmitolein, trimyristolein, trilinolein, tributyrin, tricaproin, tricaprylin, tricaprin, trilaurin, and combinations thereof.

18. The process according to claim 15 wherein, the diglyceride is selected from the group consisting of diolein and dipalmitolein.

19. The process according to claim 16 wherein, the propylene glycol ester is mixed diesters of caprylic and capric acids.

20. The process according to claim 1 or 2 wherein, the organic solvent is selected from the group comprising ethers, hydrocarbons, esters, and combinations thereof.

21. The process according to claim 1 or 2 wherein, the biologically active substance is hydrophilic and is incorporated into the first aqueous component.

22. The process according to claim 1 or 2 wherein, the emulsification of the two immiscible components is carried out using a method selected from the group consisting of mechanical agitation, ultrasonic energy, and nozzle atomization.

23. The process according to claim 1 or 2 wherein, the formation of the solvent spherules is carried out using methods selected from the group consisting of mechanical agitation, ultrasonic energy, nozzle atomization, and combinations thereof.

24. The process according to claim 1 or 2 wherein, the removing of the organic solvent is by a method selected from the group consisting of sparging, rotary evaporation, passing gas over the solvent spherules, and combinations thereof.

25. The process according to claim 1 or 2 wherein, the biologically active substance is cytarabine.

26. The process according to claim 1 or 2 wherein, the biologically active substance is morphine.

27. The process according to claim 1 or 2 wherein, the biologically active substance is hydromorphone.

28. The process according to claim 1 or 2 wherein, the biologically active substance is leuprolide.

29. The process according to claim 1 or 2 wherein, the biologically active substance is a nucleic acid.

30. The process according to claim 1 or 2 wherein, the biologically active substance is interleukin-2.

31. The process according to claim 1 or 2 wherein, the biologically active substance is amikacin.

32. The process according to claim 1 or 2 wherein, the biologically active substance is granulocyte colony stimulating factor.

33. The process according to claim 1 or 2 wherein, the biologically active substance is insulin.

34. The process according to claim 1 or 2 wherein, the biologically active substance is hepatitis B vaccine.

35. The process of claim 23 wherein, the protein is an antibody or a vaccine.

36. The process of claim 23 wherein, the antiparasitic is an antiviral or an antifungal.

37. The process according to claim 1 or 2 wherein, the biologically active substance is α-interferon.

38. The process according to claim 1 or 2 wherein, the biologically active substance is methotrexate.

39. The process according to claim 1 or 2 wherein, the biologically active substance is granulocyte-macrophage colony stimulating factor.

40. The process according to claim 1 or 2 wherein, the lipid component further comprises plant sterols.

\* \* \* \* \*